United States Patent [19]  [11] 4,266,862
Trötscher et al.  [45] May 12, 1981

[54] REFRACTOMETER FOR THE AUTOMATIC OBJECTIVE DETERMINATION OF THE REFRACTIVE CONDITION OF AN EYE

[75] Inventors: Otto Trötscher, Aalen; Erwin Wiedmann, Essingen, both of Fed. Rep. of Germany

[73] Assignee: Carl Zeiss-Stiftung, Oberkochen, Fed. Rep. of Germany

[21] Appl. No.: 853,542

[22] Filed: Nov. 21, 1977

[30] Foreign Application Priority Data

Dec. 2, 1976 [DE] Fed. Rep. of Germany ....... 2654608

[51] Int. Cl.³ .............................................. A61B 3/10
[52] U.S. Cl. ........................................ 351/14; 351/13
[58] Field of Search ............... 351/13, 14, 6; 250/206, 250/216; 356/128

[56] References Cited

U.S. PATENT DOCUMENTS

| 3,572,910 | 3/1971 | Koester | 351/13 |
| 3,819,256 | 6/1974 | Bellows et al. | 351/13 X |
| 3,824,005 | 7/1974 | Woestman | 351/13 X |
| 3,880,501 | 4/1975 | Munnerlyn | 351/13 X |
| 3,883,233 | 5/1975 | Guilino | 351/6 |
| 4,125,320 | 11/1978 | Rassow | 351/13 |

Primary Examiner—John K. Corbin
Assistant Examiner—Rodney B. Bovernick
Attorney, Agent, or Firm—Hopgood, Calimafde, Kalil, Blaustein & Lieberman

[57] ABSTRACT

The invention contemplates a refractometer that images a test mark on the retina and is automatic in its determination of both refractive-power and astigmatism parameters, for the eye under examination. An imaging lens serves both (1) to project the test mark to the retina and (2) to convey that image for refocus external to the eye, to a scanner having the ability to digitally establish the eye's focal length. In the process of establishing the eye's focal length, the instrument automatically positions the imaging lens to best serve infinity viewing by the eye, and a prism then rotates the test mark while the scanner photoelectrically tracks the refocused image for the angles at which response is at a maximum, thus establishing astigmatism parameters. The instrument provides selective direct indication or print-out of the automatically determined parametric values.

16 Claims, 4 Drawing Figures

REFRACTOMETER FOR THE AUTOMATIC OBJECTIVE DETERMINATION OF THE REFRACTIVE CONDITION OF AN EYE

The present invention relates to a refractometer for the automatic objective determination of the refractive condition of an eye wherein a test mark is focused by an optical image-producing system on the retina of the eye to be examined, and wherein light reflected from the retina, after passing through the same image-producing system and before reaching the test mark, is mirror-deflected toward a photoelectric receiver having a scanning device.

Such a refractometer is known from West German Patent Application No. 1,955,859. In said refractometer, the signal produced by the photoelectric receiver is used directly to vary the refractive power of an optical system arranged in front of the eye being examined, until said signal disappears. Until the present time, there has been practically no optical system whose refractive power can be changed continuously and with the necessary precision; therefore, one has been forced, in practice, to have recourse to intermittently operating systems, namely so-called phoropters. In these systems, lenses of different power of refraction are brought, one after the other, in front of the eye being examined; however, this technique necessarily means a dark phase upon each change of lens, and such dark phases interfere with the accommodation of the eye being examined.

The known refractometer also permits the determination of astigmatism, but this is a relatively cumbersome procedure.

Automatically operating refractometers are also known in which a displaceable test mark is focused in an image-forming beam on the retina of the eye being examined, and in which the retina image is focused on a similar test mark in a separate observation beam. Behind said test mark there is arranged a photoelectric receiver, and the marks in the imaging and observation beams are displaced synchronously until the receiver signal reaches a maximum. In order to be able to measure, in the course of a determination of astigmatism, in different principal planes of the eye, the two test marks must be turned synchronously. Since the synchronous displacement and rotation of elements in separate light beams results in large problems of synchronism, the optical and mechanical expense involved in such refractometers is very great.

An object of the present invention is to provide a refractometer for the automatic objective determination of the condition of refraction of an eye, which makes possible, without great expense, both an undisturbed determination of the spherical defect of the eye and of the antigmatism. Further, it is an object to provide such a refractometer in which the entire pupil of the eye is used for refractioning, and which makes it possible to eliminate disturbing reflection signals.

These objects are achieved, in accordance with the invention, by the combination of the following features:

(a) the image-producing system contains a first lens and a second lens, between which there is a parallel-ray path, and these lenses produce a first intermediate image of the test mark; in addition, a third lens cooperates with the lens of the eye to produce a second intermediate image of the test mark on the retina of the eye;

(b) between the first and second lenses there is provided a partially transmitting mirror and, in the light path of the latter, a lens which corresponds to the first lens of the image-producing system in such manner that light reflected from the retina produces a third intermediate image of the test mark outside the illumination beam;

(c) at the locus of this third intermediate image, there is arranged a scanning device which, together with a photoelectric receiver arranged behind same, produces a signal which is modulated in accordance with the position of the intermediate image;

(d) using the output of the photoelectric receiver, there is provided circuitry which converts the modulated signal into a control signal that is proportional to the deviation of the third intermediate image from the theoretically proper position;

(e) one of the lenses of the image-producing system is displaceable by means of a positioning motor which is operated by the control signal.

The eye to be examined is fixed with respect to the direction of view and accommodation, as by looking at a vision-testing chart. For the measurement itself, infrared light, which is not observed by the eye, is used in known fashion.

In the new refractometer, all elements necessary for the formation of an image are common to the formation of the image and to the observation. For measurement, one of the lenses, preferably the second lens of the image-producing system, is displaced by the motor until the control signal fed to the motor achieves a value of zero. At this moment, the second intermediate image of the test mark is produced on the retina of the eye, and the third image which has been segregated is conjugate to the test mark. The new refractometer thus operates in accordance with the very precise and error-free principle of null-finding.

The new refractometer permits of a simple determination of astigmatism. For this purpose, a reversing prism, preferably a Dove prism, is mounted for rotation about the optical axis in the parallel beam between the first and second lenses of the image-producing system. Upon rotation of this prism, the intermediate image of the test mark is rotated. Since the observation beam also passes through the prism, the position of the test image at the place of the scanning device remains unchanged, regardless of the angle of rotation of the prism.

During rotation of the reversing prism, and if astigmatism is present, the motor (actuated by the control signal) will endeavor constantly to displace the lens of the image-producing system in such manner that a state of balance is maintained. When the point of reversion in the displacement of the lens is reached, this point corresponds to the principal plane. A reading is made (a) of diopters and (b) of the axial position indicated by the angle of rotation of the prism. Thereupon, the split image is turned 90° by the prism, and the measurement values determined in this position are read off. It is, of course, also possible to operate automatically with a continuously rotating prism and to use electronic-circuitry to identify (a) the angle at which said reversion occurs and (b) the angle which is 90° displaced therefrom.

With the new refractometer, it is advisable to provide, between the deflection mirror (which serves to single-out the reflected light) and the photoelectric receiver, a scanning device which consists of two motor-driven rotating semi-circular screen disks, which are axially spaced apart from each other and displaced 180° with respect to each other, the screen disks being so arranged that in the balanced condition the third intermediate image of the test mark lies at the axial midpoint between the two screen disks. When a slit-shaped test image is used, each screen disk is advisedly so devised that it contains screen slits whose sides correspond to that of the third intermediate image and which follow each other in a 1:1 scanning ratio. The reflection coming from the cornea of the eye being examined then extends, on each screen disk, over a plurality of screen slits which, together with the solid (unslitted) portions in between, form a 50% filter so that light modulation attributable to this disturbing reflection is practically zero. The same is true also of other disturbing reflections from the optical beam. The resultant noise signal may be readily separated from the periodic useful signal by electronic means, and filters may be provided as needed to remove harmonics of the disturbing signal.

In the new refractometer, only extremely little light is reflected by the retina of the eye being examined, so that it is essentially a question of excluding, in addition to the corneal reflection, also the reflections produced on the surfaces of the optical elements in the ray path. For this purpose, it is advantageous to arrange the second and third lenses of the illuminating beam at an inclination to the optical axis. If these lenses form an angle of, for instance, 8° with the optical axis of the refractometer, then the reflections produced on the lens surfaces will be deflected out of the ray path and will no longer form a disturbing signal.

Refraction values determined by the new refractometer may be used for the direct or indirect control of a subsequent device for the subjective determination of spectacle lenses, for example, a phoropter. Such a digitally controllable phoropter can therefore be connected "on-line" with the new refractometer, whereby automatically determined values are automatically set. It is also possible to operate "off-line", in which case the refractometer may deliver the automatically determined measured values via a data-bearing device, for instance a punched card, which is introduced into the phoropter before the subsequent subjective determination of the initial adjustment.

The invention will be described in further detail below with reference to the accompanying drawings, in which.

Figure 1:
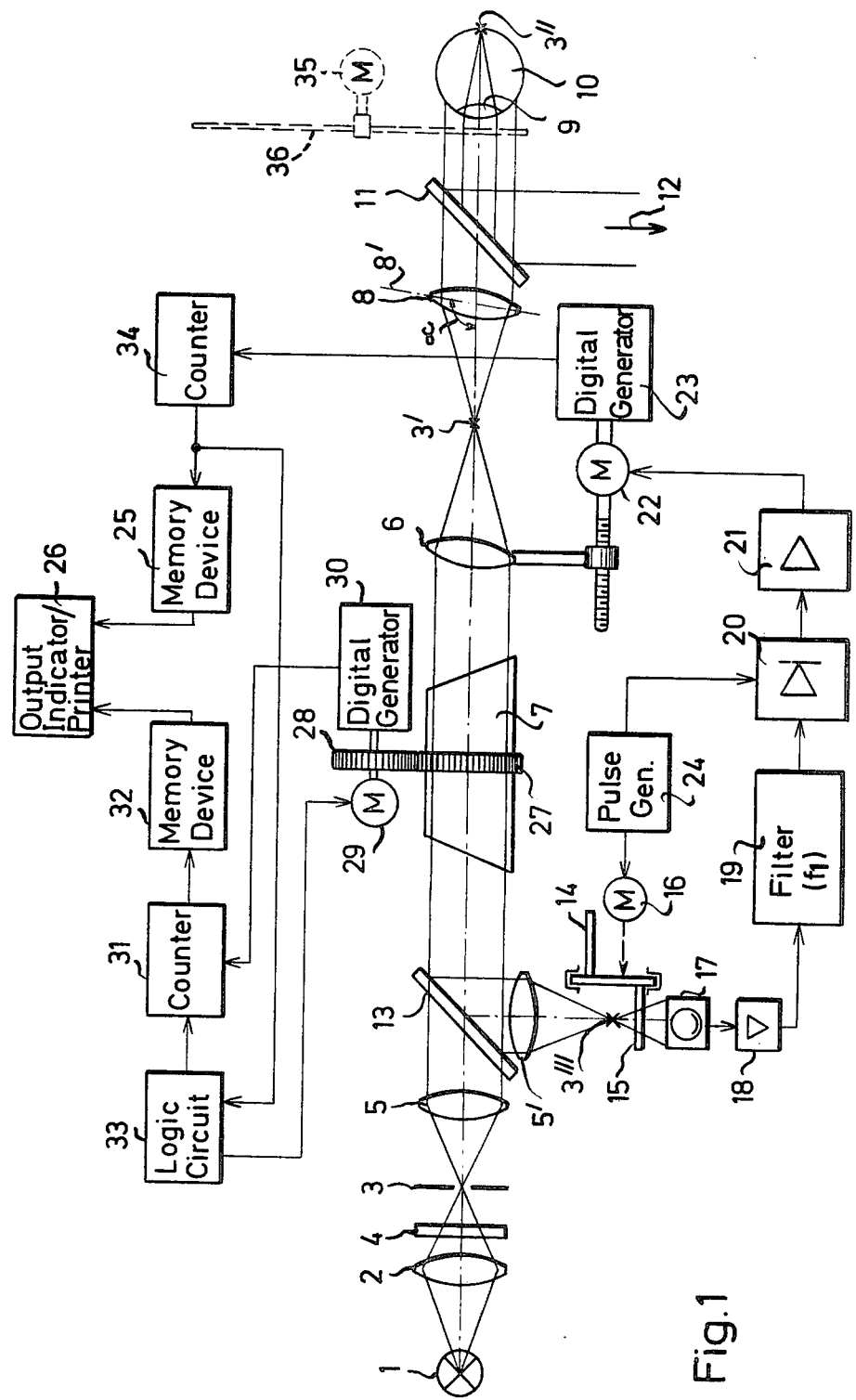
FIG. 1 is a diagram schematically showing one embodiment of the new refractometer.

In FIG. 1, 1 is a source of light which, via a condenser 2, illuminates a test mark 3 in the form of a slit. A filter 4 arranged in front of the test mark 3 permits the passage only of infrared light. The test mark 3 is focused at infinity by a collimating lens 5; and a second such lens 6 produces a first intermediate image 3' of the test mark. In the parallel-light region between the lenses 5 and 6, a reversing or Dove prism 7 is positioned for rotation about the optical axis, and a partially transmitting deflection mirror 13 is shown between lens 5 and prism 7.

In FIG. 1, the focusing elements have been shown as simple lenses for ease of illustration. Actually, they are lens systems, so that the word "lens" as used below should be understood to additionally include lens systems.

In front of the eye 10 to be examined, a lens 8 is arranged, fixed in space, in such a manner that its image-side focal point F' coincides with the object-side principal plane of the eye lens 9. This principal plane, in the case of an eye which is accommodated to infinity, lies about 2 mm behind the corneal vertex. In the case of an eye with normal vision, the lens 8, in cooperation with the eye lens 9, produces a second intermediate image 3" of the test mark on the retina of the eye.

In front of the eye 10 there is arranged a partially transmitting mirror 11 via which light in the visible wavelength region is reflected into the eye from a target, for instance, a vision-testing chart. The eye is thus fixed with respect to the direction of view, as is indicated by the arrow 12; at the same time, accommodation of the eye is achieved by the target which is mirrored therein.

Between lenses 5 and 6 of the image-producing system, the partially transmitting mirror 13 and an associated lens 5' (corresponding to the lens 5) focus light reflected from the retina of the eye 10 at a third intermediate test-mark image 3''', outside the illumination beam. At the locus of intermediate image 3''', there is provided a scanning device consisting of two semicircular screening disks 14–15 which are axially spaced apart and angularly offset 180° with respect to each other; disks 14–15 are rotated by motor means 16 and are so positioned that in balanced condition the intermediate image 3''' lies at the axial midpoint between the two screening disks 14–15. Light passing through these screening disks falls on a photoelectric receiver 17.

Figure 2:
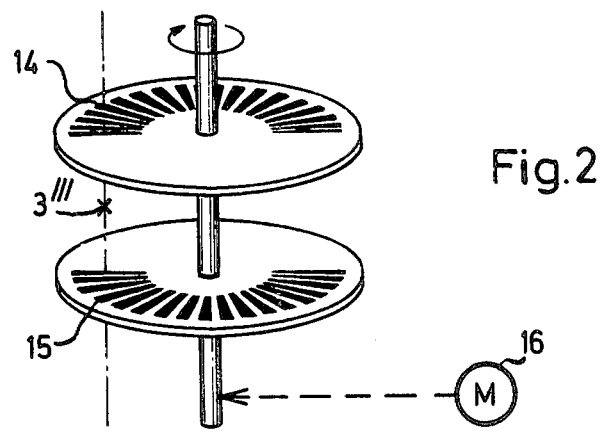
FIG. 2 is a simplified perspective view of the scanning device employed in the refractometer of FIG. 1.

As can be noted from FIG. 2, each screening disk 14–15 consists of a transmission screen in the form of screen slits which extend, in the example shown, over half a circle. The other half of the circle of each screening disk is fully transparent. It is also possible to develop each screening disk such that the transmission screen extends only over a quarter of a circle and to make the remaining quarter of a circle opaque. In this way, dark intervals are obtained in interlace with scanning intervals, and the dark intervals may be used in the electronic section for accommodation of a signal or for like purposes.

Figure 3A:
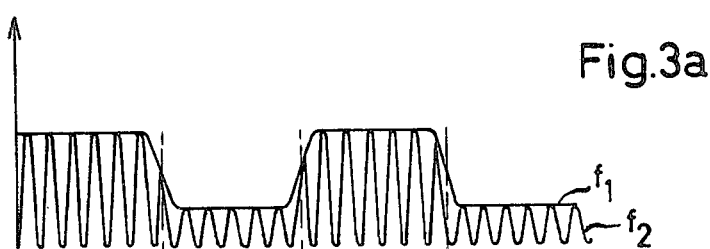
FIGS. 3a and 3b are plots of waveform to show the signals supplied by the photoelectric receiver of the refractometer in different measurement positions.

When the eye 10 which is to be examined is not of normal vision, the intermediate image 3" is not produced on the retina, and the third intermediate image 3''' does not lie precisely at the midpoint between the two screening disks 14–15, in which case the signal supplied by the photoreceiver 17 is as illustratively shown in FIG. 3a. Such a signal is characterized by a frequency $f_2$ which is determined by the screen constant and the rotational speed of the disks 14–15. This signal is further characterized by amplitude-modulation at the frequency $f_1$, wherein the signal section 14', for instance, is produced when light is interrupted by the screening disk 14, and wherein the signal section 15' is produced when light is interrupted by the screening disk 15. The signal of FIG. 3a will thus be seen to be modulated in accordance with the instantaneous position of the intermediate image 3''', and to the extent that such position is axially offset from the midpoint between disks 14–15. The signal output of the photoreceiver 17 is supplied to an amplifier 18 and thence to a filter 19 which passes only the frequency $f_1$. This actual measurement signal is then phase-sensitively rectified at 20, using the synchronizing or phase-reference signal from a timing-pulse generator 24, and is thus converted into a control signal which is proportional to the instantaneous deviation of the third intermediate image 3''' from the theoretically proper midpoint position. This control signal is amplified at 21 and is then supplied to a positioning motor 22 which displaces the second lens 6 of the image-producing system in the direction of the optical axis. In the form shown, a digital generator 23 connected to the shaft of motor 22 produces a digital signal which is proportional to the instantaneous position of lens 6.

Depending upon the optical arrangement selected, the position of lens 6 is proportional to the diopter value of the eye 10. With a lens 8 of focal length f=50 mm, a diopter range of ±20 diopters can be covered by the lens 6.

Figure 3B:
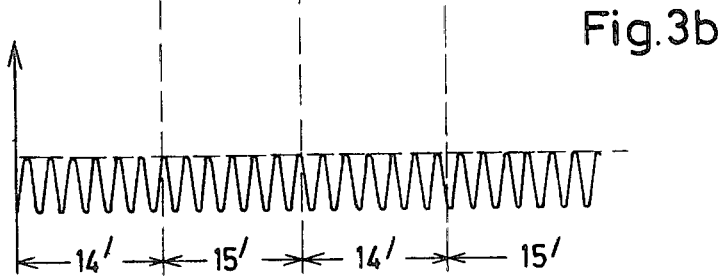

In case of an eye 10 with defective vision, a control signal is produced which displaces the lens 6 until the intermediate image 3'' is produced on the retina of the eye. At this moment, the third intermediate image 3''' is produced at the midpoint between the two screening disks 14–15, and the signal produced by the photoreceiver 17 has the shape shown in FIG. 3b. As can be noted, the control signal of frequency $f_1$ has disappeared, and motor 22 thus comes to rest. The corresponding digital signal (at 23) is now fed via a counter 34 and a memory device 25 to an output unit 26 which serves to indicate, print out, or deliver an encoded data-bearing device, such as a suitably punched card.

The reversing prism 7 is rotatable about the optical axis by gear means 27–28, the same being driven by a motor 29 having a digital position generator 30 coupled thereto. Generator 30 produces a signal which is proportional to the instantaneous rotary position of prism 7; when a balance position is achieved, the digital output of generator 30 is fed via a counter 31 and a memory device 32 to the output unit 26.

For the determination of refraction, the reversing prism 7 is first of all held in its starting position. As soon as the lens 6 has come to rest, a logic circuit 33 is caused, via counter 34, to operate the motor 29, thus rotating reversing prism 7. If the eye 10 to be examined suffers from astigmatism, the balancing electronic system endeavors, upon rotation of prism 7, to retain the condition of balance, which is effected by corresponding movement of the lens 6. In this connection, the diopter reading changes continuously, and the logic circuit 33 checks when the point of reversal of this reading is reached. This position corresponds to a principal plane. Under control from the logic circuit 33, the axial position is then indicated via counter 31, and the diopter value is indicated by counter 34. Thereupon, the slit image 3' is displaced 90° by the prism 7, and lens 6 is driven by means 17-20-22 until a new balance is obtained. The values for axis and diopter obtained at this new balance position are also included in the output reading at 26.

Instead of the step-by-step manner of operation described, when examining for astigmatism, it is also possible to use a continuously rotating prism 7, output readings being keyed by operation of logic circuit 33, upon noted occurrence of reversal of the direction of diopter change. In this case diopter value and axial position (of lens 6) are included in the output indication at 26, for each occurrence of a point of reversal of the diopter indication.

With the refractometer shown, it is important to eliminate the optical-element reflections produced in the ray path, e.g., surface reflections between optical elements. For this purpose, the lenses 6 and 8 are shown inclined to the optical axis of the illuminating system. These lenses are so designed that, despite their oblique position, errors in imaging are avoided. In the case of the oblique position shown for lens 8, its vertical axis 8' forms with the optical axis an angle α which has a value of, for instance, 8°. Thus, the result is obtained that reflections which are produced on the surfaces of the lens 8 are deflected outwardly, i.e., such reflections cannot be passed to the screening disks 14–15.

However, reflection from the cornea of the eye 11 does reach the screening disks 14–15. But such reflection has such a position and size that, as already indicated above, it produces only an easily separated d-c component of the light reaching disks 14–15.

FIG. 1 indicates another way of separating the useful signal from the reflection signals of the optical system. As shown in dashed lines, an interrupter disk 36 is provided for this purpose, and is driven by a motor 35 to periodically interrupt the light which arrives at the eye. The frequency of interruption is selected to be greater than the scanning frequency which characterizes the screening disks 14–15. One thus obtains an alternating signal of high frequency which comes from the eye 10 and which is superimposed on the low-frequency scanning signal. It is very simple, by electrical means, for instance by a second frequency filter interposed behind the frequency filter 19, to filter out the high-frequency measurement signal and thus to obtain a control signal which is associated with the retinal image and has but one undesired component, namely that associated with corneal reflection. The corneal reflection, as already mentioned, may be eliminated by selecting the periodicity of the screens 14–15 in accordance with the size of the reflection image.

What is claimed is:

1. Refractometer for the automatic objective determination of the condition of refraction of an eye, in which a test mark is focused by an optical image-producing system on the retina of the eye to be examined and the light reflected from the retina after passing through said image producing system and before reaching the test mark is reflected to a photoelectric receiver provided with a scanning device, characterized by the combination of the following features:

(a) the image-producing system contains a first lens and a second lens between which there is a parallel beam path and which produce a first intermediate image of the test mark, as well as a third lens which, in combination with the eye lens, produces a second intermediate image of the test mark on the retina of the eye;

(b) between the first and second lenses a partially transmitting mirror is arranged and, in the light-path of the latter, a lens corresponding to the first lens of the image producing system in such a manner that the light reflected by the retina produces a third intermediate image of the test mark outside the path of the illumination beam;

(c) at the location of this third intermediate image there is provided a scanning device which, together with a photoelectric receiver arranged behind it, produces a signal which is modulated in accordance with the position of the intermediate image;

(d) behind the photoelectric receiver there is provided an arrangement which converts the modulator signal into a control signal which is proportional to the deviation of the third intermediate image from the theoretical desired position;

(e) one the lenses of the image producing system is displaceable by means of a motor (22) to which the control signal is fed.

2. Refractometer according to claim 1, characterized by the fact that the second lens of the image producing system is displaceable in the direction of the optical axis.

3. Refractometer according to claims 1 or 2, characterized by the fact that a reversing prism turnable about the optical axis is arranged between the first two lenses of the image-producing system.

4. Refractometer according to claim 3, characterized by the fact that for the rotating of the reversing prism there is provided a motor which is controlled via logic-circuit means which is connected with the arrangement for producing the control signal.

5. Refractometer according to claim 4, characterized by the fact that the said logic-circuit means with determined point of reversal of the control signal releases the corresponding position of rotation of the reversing image as a digital output signal.

6. Refractometer according to claim 1, characterized by the fact that an illuminated slit is used as test mark.

7. Refractometer according to claim 1, characterized by the fact that between the photoelectric receiver and the partially transmitting mirror which serves for the mirroring-out of the reflected light there is provided a scanning device which consists of two semi-circular screening disks which are spaced apart from each other and shifted 180° with respect to each other, they being rotated by means of a motor and being so arranged that in balanced condition the third intermediate image lies in the center between the two screening disks.

8. Refractometer according to claim 7, characterized by the fact that each screening disk consists of a transmission screen in the form of screen slits whose size corresponds to that of the third intermediate image and which follow each other in a 1:1 scanning ratio.

9. Refractometer according to claims 1 or 2, characterized by the fact that the second lens and the third lens of the image producing system are arranged inclined to the optical axis of said system.

10. Refractometer according to claim 1 characterized by the fact that in front of the eye being examined there is arranged a light modulator which periodically interrupts the beam of light and the frequency of interruption of which is greater than the scanning frequency of the scanning device.

11. Refractometer according to claim 1, characterized by the fact that the automatically determined refraction values are used, directly or indirectly, to control a subsequent device for the subjective determination of spectacle lenses.

12. Refractometer according to claim 11, characterized by the fact that the automatically determined refraction values are delivered via data bearing means such as a punched card.

13. Refractometer according to claim 1, wherein the optical image-producing system includes a light source limited to the infrared.

14. The method of automatically determining the refractive condition of an eye, which comprises producing a first intermediate image of a test mark by means of spaced first and second lenses which establish a parallel-beam path therebetween, producing a second intermediate image of the test mark on the retina of the eye by means of a third lens and the lens of the eye, producing a third intermediate image of the test mark by means of a fourth lens outside the light path between the test mark and the eye and by partially reflecting retina-reflected light to the fourth lens, the partial reflection being from within the parallel-beam path between the first and second lenses, photoeletrically producing a signal which is modulated in accordance with the instantaneous position of the third intermediate image, converting the modulated signal to a control signal which is proportional to the deviation of the third intermediate image from its theoretical desired position, and using the control signal to axially displace one of the first three lenses in the direction which reduces the modulating signal.

15. The method of claim 14, in which an output signal proportional to the instantaneous axial position of the displaced lens is developed upon disappearance of the modulating signal.

16. The method of claim 14, in which the images of the test mark are produced with light limited to the infrared.

* * * * *